US00PP20446P2

(12) United States Plant Patent

Deng et al.

(10) Patent No.: US PP20,446 P2

(45) Date of Patent: Nov. 3, 2009

(54) *CALADIUM* PLANT NAMED 'SUMMER ROSE'

(50) Latin Name: *Caladium×hortulanum*
Varietal Denomination: Summer Rose

(75) Inventors: Zhanao Deng, Wimauma, FL (US); Brent Harbaugh, Wimauma, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 18 days.

(21) Appl. No.: 12/151,985

(22) Filed: May 12, 2008

(51) Int. Cl.
*A01H 5/00* (2006.01)

(52) U.S. Cl. ..... Plt./373

(58) Field of Classification Search ..... Plt./373
See application file for complete search history.

(56) References Cited

OTHER PUBLICATIONS

Deng Ziaanao et al. Proceedings of the 119th Annual meeting of the Florida State Horticultural Society. Proceedings of the Florida State Horticultural Society 119 p. 409-412. 2006, abstract.*

* cited by examiner

*Primary Examiner*—Annette H Para

(57) ABSTRACT

A distinct cultivar of *Caladium* plant named 'Summer Rose', characterized by its very large heart shaped leaves, bright rose color, and demonstrated potential to produce large plants with huge leaves when grown in outdoor landscapes and attractive plants when forced in pots.

1 Drawing Sheet

BACKGROUND OF THE INVENTION

'Summer Rose' was a seedling initially evaluated in 2001 as GC607 originating from the cross-pollination of the *Caladium×hortulanum* cultivar 'Aaron' with the seedling GCREC-S25 (an unnamed breeding line from our breeding program) made in a greenhouse in Bradenton, Fla. GCREC-S25 was from across of 'Fire Chief'×'Torchy'. Aaron is a white, fancy, and heart-shaped leaf *caladium* cultivar selected for its large leaves and plant vigor. 'Fire Chief' and 'Torchy' were selected for their vivid red veins and interveinal areas. GCREC-S25 was selected for its vigor and bright color. Ancestry of 'Aaron', 'Fire Chief' and 'Torchy' are unknown. Asexual propagation by tuber division was done in Bradenton, Fla. and Dover, Fla. Evaluation in field and pot studies since 2001 have shown that the unique features of this new *Caladium* plant are stable and reproduced true to type in successive generations of asexual propagation.

SUMMARY OF THE INVENTION

The new *Caladium* has not been observed under all possible environmental conditions. The phenotype may vary somewhat with variations in the environment such as light intensity and temperature, without, however, any variance in genotype.

*Caladiums* are utilized in the ornamental industry as potted plants and landscape plants. They have a diversity of leaf colors that arise from red, pink, and white pigments displayed in solid, spot, and/or blotch patterns in interveinal areas. Veins and leaf margins may be colored or green adding to the diversity of patterns. For plants to be successful in the landscape, they must be vigorous, brightly colored, and have large leaves (unless used for border plants such as is the case for strap or lance leaved cultivars). When forced in containers to be used as an ornamental potted plant, shorter plants with many leaves that emerge quickly are desirable traits. The new *caladium* plant, 'Summer Rose', has a distinct rose color in the leaf center (venation and interveinal areas) surrounded by a green margin speckled with white. It's predominantly rose colored leaves make it very different from 'Aaron', the female parent, which has white leaves. It is different in color from 'GCREC-S25', the male parent, which has red leaves. 'Summer Rose' has performed well when forced in pots, and in landscape settings in a number of trials showing the height, leaf size, and vigor necessary for landscape use. Tuber production, a necessary consideration for commercialization of a cultivar by the *caladium* tuber producing industry, has been excellent with tubers produced in the ideal sizes as described in the description section.

BRIEF DESCRIPTON OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description, which accurately describe the colors of the new *Caladium*.

The photograph, labeled FIG. 1, illustrates the overall appearance of the new cultivar, Summer Rose. The photograph is a side perspective view of a typical plant of 'Summer Rose' grown in a container.

DETAILED BOTANICAL DESCRIPTION

The following is a detailed description of the new variety with color terminology in accordance with British Color Council and The Royal Horticultural Society, Horticultural Colour Chart, except where general color terns of ordinary dictionary significance are obvious. Wherein dimensions, sizes, and other characteristics are given, it is to be understood that such characteristics are approximations of averages set forth as accurately as practicable. The description herein is from 4 month old specimens grown in Bradenton, Fla., in 2003–2005. Plants used for describing color were grown in 15 cm containers in a 40% shaded greenhouse from Jumbo (6.4 to 8.9 cm diameter) de-eyed tubers.

Botanical classification: *Caladium×hortulanum* cultivar Summer Rose.

Propagation:

*Type.*—By tuber division.

*Time to develop roots and sprout.*—42 days (Spring −15° C. night to 29° C. day). 18 days (Summer −21° C. night to 35° C. day).

*Root description.*—Dense, moderately thick roots (up to 2.5 mm at the basal end) with little branching and few lateral roots.

Plant description:

*Plant shape.*—Upright, symmetrical.

*Plant height.*—About 52 cm from top of soil to top of leaf plane 4 months from planting tubers in ground beds in full sun.

*Leaf blade.*—Leaves are peltate, sagitate-cordate, with palmate-pinnate venation 29–33 cm long and 19–23 cm wide. The center veins are red-purple (RHS 61A). The upper surface has a dark green (RHS 137A) irregular margin, 3–9 mm wide, bordering the entire leaf except for the basal leaf sinus where it is grayed-purple (RHS 185A). Interveinal areas in the center of the leaf are red-purple (RHS 60D) but this is bordered by a green-white (RHS 157D) speckling on a green background (RHS 147A). The undersurface is predominantly a grayed-purple (RHS 186B) with very little of the upper leaf color pattern showing through. The margin is green (138A).

*Petiole.*—Petioles are 3–4 mm and are a red-purple at the leaf attachment and gradually darken to a brown (2000A) at the petiole base.

*Tuber.*—Tubers are multi-segmented; a tuber 6.4–8.9 cm in diameter will typically bear 3–4 dominant buds. Tuber surfaces are brown (RHS 200B–C) with the cortical area very light yellow (RHS 4D center to 8D edge).

*Inflorescence.*—The flowering and reproductive organs do not differ in character from other *caladium* plants.

Performance: 'Summer Rose'= was evaluated for tuber production and plant performance at the Gulf Coast REC — Bradenton, Fla. during 2003 and at Dover, Fla. in 2004. The soil was an EauGallie fine sand with about 1% organic matter and a pH of 6.2. Plants were grown in a plastic-mulched raised-bed system maintaining a constant water table with seep irrigation. The beds were 91 cm wide and 20 cm high with 2.54 cm *caladium* seed pieces planted 15 cm apart in 3 rows (Bradenton) or 2 rows (Dover) also spaced 15 cm apart. Osmocote 18N-2.6P-10K 8–9 month controlled release fertilizer was applied to the bed surface when shoot tips were emerging from the soil with N at 336 $kgXha^{-1.}$ Plots were organized in a randomized complete block design consisting of three replications. For tuber production, each plot was 1.2 $m^2$ and contained 30 propagules. An analysis of variance was conducted in order to compare the performance of >Summer Rose= to its parents and other important other commercially important white fancy-leaf cultivars. For plant performance in the landscape, three plants were measured in the center of each plot and plant height, leaf number, and leaf size were measured mid-summer. Since year did not significantly influence plant performance, the data was averaged over the 2 years.

'Candidum' is ranked as one of the best cultivars for tuber production and tuber producers consider it very profitable to grow because it yields so well. 'Summer Rose' tuber production was excellent with tuber weights nearly 1.3 and 1.6 times higher than 'Candidum' in 2003 and 2004, respectively (Table 3). Its production index (an economic indicator of crop value) was also greater than 'Candidum' in both years (1.3 or 1.4 times greater). Similarly, 'Summer Rose' had higher yields than 'Rosebud' as seen in tuber weight (1.3 and 1.8 times higher) and production index (1.2 and 1.3 time higher) measurements. Although the same number (30) of seed pieces were planted per plot, more than 30 tubers were harvested. This occurs since several sprouts may emerge per seed piece and result in more than one tuber developing per planted seed piece, and also because tubers can break apart during harvest. If tubers are marketable, these factors can increase profitability. Although 'Summer Rose' did not have the greatest number of marketable tubers, it had 40 tubers per plot and had similar or more tubers than other cultivars tested. There were also a greater percentage of tubers in the mammoth and jumbo grades compared to 'Rosebud' and 'Carolyn Whorton', and these grades have the high market value.

Landscape performance of cultivars grown under full-sun conditions was evaluated in 2003 and 2004 on the same plots used for evaluating tuber production. Plant height, number of leaves, and foliar characteristics were recorded approximately 4 months after planting (Table 1). 'Summer Rose' was taller with larger leaves than 'Rosebud' but similar in height and leaf size to 'Candidum' and 'Carolyn Whorton'. It had excellent performance ratings all through the growing season.

'Summer Rose' tubers were forced in 10-cm containers and its growth compared to three pink-fancy commercial cultivars. No. 1 tubers were planted in a peat/vermiculite mix on Jun. 24, 2002. The study was conducted in a glasshouse with 50% light exclusion during the summer in Bradenton, Fla. Average daily temperatures ranged from a low of 21° C. night to 29° C. day during the experiment. Plant height, number of leaves, and foliar characteristics were recorded 7 weeks after planting.

Plant performance of 'Summer Rose' in containers was similar to the other cultivars tested. Noticeable differences included that the number of days-to-sprout was less for 'Summer Rose' than 'Rosebud' for de-eyed tubers, and plant height for de-eyed 'Summer Rose' was greater than 'Rosebud'. Since 'Rosebud' is known as an excellent pot plant, these results indicate 'Summer Rose' also has potential for use as a potted/container plant.

TABLE 1

Plant performance approximately 4 months from planting 2.54 cm tuber propagules in ground beds in full sun in 2003 and 2004. Values presented are means of three replications with three plants measured per plot per year, averaged over 2 years.

| | Plant | Leaf | | | Overall | | |
|---|---|---|---|---|---|---|---|
| | height | | length | width | performance rating[z] | | |
| Cultivar | (cm) | number | (cm) | (cm) | Early | Mid | Late |
| Candidum | 46 | 13 | 28 | 18 | 3.3 | 3.7 | 3.5 |
| Carolyn Whorton | 48 | 16 | 33 | 22 | 3.0 | 4.6 | 4.5 |
| Rosebud | 42 | 20 | 23 | 16 | 2.5 | 3.2 | 2.0 |
| Summer Rose | 52 | 17 | 31 | 21 | 4.5 | 4.5 | 4.5 |
| LSD ($\alpha = 0.05$) | 8.2 | 5.3 | 2.2 | 1.7 | 1.0 | 0.7 | 0.1 |

[z]Overall plant performance was rated Jul. 22 (early), Aug. 31 (mid), and Nov. 16 (late), 2004.

TABLE 2

Plant performance for *caladium* cultivars grown in 10-cm containers in a 25% shaded glasshouse, 2005, Bradenton Florida. Values represent the means of eight plants produced from intact (I) or de-eyed (D) No. 1 tubers (3.8 to 6.4 cm in diameter) planted individually per container.

| | Sprout (days)[z] | | Plant ht (cm) | | Leaf (no.) | | Leaf length (cm) | | Leaf width (cm) | |
|---|---|---|---|---|---|---|---|---|---|---|
| Cultivar | I | D | I | D | I | D | I | D | I | D |
| Calypso | 14 | 13 | 39 | 40 | 11 | 19 | 25 | 20 | 18 | 14 |
| Carolyn Whorton | 20 | 18 | 43 | 41 | 10 | 14 | 27 | 21 | 18 | 14 |
| Rosebud | 20 | 23 | 38 | 32 | 12 | 19 | 24 | 17 | 13 | 13 |
| Summer Rose | 18 | 17 | 36 | 39 | 9 | 22 | 25 | 21 | 19 | 16 |
| LSD ($\alpha$ = 0.05) | 4.5 | 4.4 | ns | 4.5 | ns | ns | ns | ns | ns | ns |

[z]Number of days from planting to the first unfurled leaf.

TABLE 3

Caladium tuber characteristics from cultivars harvested in 2003 and 2004. Values presented are means of three replications with 30 propagules per 1.2-m2 plot per year.

| | Tuber | | | | | | | |
|---|---|---|---|---|---|---|---|---|
| | | | Marketable | Tuber distribution[z] (%) | | | | |
| | Weight (g) | P.I.[y] | (number) | Super mam | Mam | bo | No. 1 | Jumbo No. 2 |
| | | | Year 2003 | | | | | |
| Candidum | 2784 | 98 | 33 | 1 | 12 | 30 | 43 | 14 |
| Carolyn Whorton | 2879 | 101 | 39 | 0 | 9 | 28 | 40 | 24 |
| Rosebud | 2632 | 109 | 45 | 0 | 4 | 24 | 45 | 27 |

TABLE 3-continued

Caladium tuber characteristics from cultivars harvested in 2003 and 2004. Values presented are means of three replications with 30 propagules per 1.2-m2 plot per year.

| | Tuber | | | | | | | |
|---|---|---|---|---|---|---|---|---|
| | | | Marketable | Tuber distribution[z] (%) | | | | |
| | Weight (g) | P.I.[y] | (number) | Super mam | Mam | bo | No. 1 | Jumbo No. 2 |
| Summer Rose | 3519 | 126 | 40 | 0 | 8 | 47 | 40 | 5 |
| LSD ($\alpha$ = 0.05) | 306 | 25 | 13 | 2 | 13 | 19 | 26 | 17 |
| | | | Year 2004 | | | | | |
| Candidum | 2860 | 96 | 35 | 2 | 6 | 27 | 54 | 12 |
| Carolyn Whorton | 4268 | 132 | 53 | 0 | 9 | 20 | 45 | 26 |
| Rosebud | 2553 | 102 | 49 | 0 | 2 | 18 | 47 | 33 |
| Summer Rose | 4597 | 132 | 40 | 0 | 15 | 42 | 32 | 12 |
| LSD ($\alpha$ = 0.05) | 531 | 15 | 9 | 2 | 9 | 16 | 21 | 14 |

[z]Tubers graded by maximum diameter; No. 2 (2.5-3.8 cm), No. 1 (3.8-6.4 cm), Jumbo (6.4-8.9 cm), Mammoth (mam = 8.9-11.4 cm), and Super Mammoth (super mam = >11.4 cm).
[y]The production index (PI) is an indicator of economic value of harvested tubers calculated as: N (No. 2s) + 2N (No. 1s) + 4N (Jumbos) + 6N (Mammoth) + 8N (Super Mammoth); where N = number of tubers in each grade.

It is claimed:

1. A new and distinct cultivar of *Caladium* plant named 'Summer Rose', as illustated and described.

* * * * *

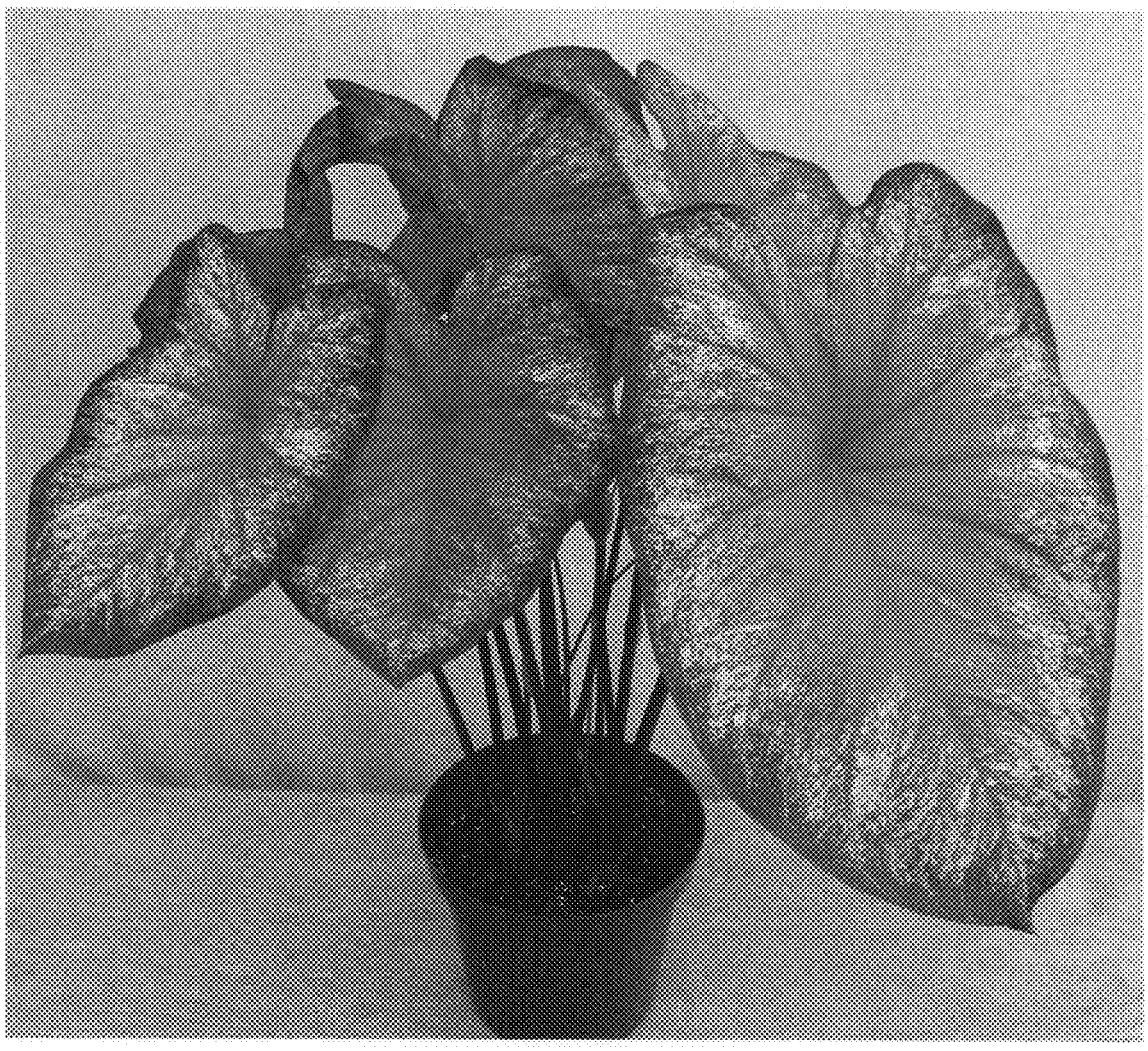
Fig. 1 – Caladium Plant named 'Summer Rose'